(12) United States Patent
Hayes et al.

(10) Patent No.: US 11,439,504 B2
(45) Date of Patent: Sep. 13, 2022

(54) REPLACEMENT HEART VALVE WITH IMPROVED CUSP WASHOUT AND REDUCED LOADING

(71) Applicant: BOSTON SCIENTIFIC SCIMED, INC., Maple Grove, MN (US)

(72) Inventors: Michael G. Hayes, Galway (IE); Tara Hogan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 137 days.

(21) Appl. No.: 16/870,266

(22) Filed: May 8, 2020

(65) Prior Publication Data

US 2020/0352708 A1 Nov. 12, 2020

Related U.S. Application Data

(60) Provisional application No. 62/846,018, filed on May 10, 2019.

(51) Int. Cl.
*A61F 2/24* (2006.01)

(52) U.S. Cl.
CPC .......... *A61F 2/2418* (2013.01); *A61F 2/2412* (2013.01); *A61F 2/2415* (2013.01); *A61F 2220/0008* (2013.01); *A61F 2220/0075* (2013.01); *A61F 2250/0024* (2013.01); *A61F 2250/0069* (2013.01)

(58) Field of Classification Search
CPC ... A61G 2/2412; A61G 2/2415; A61G 2/2418
See application file for complete search history.

(56) References Cited

U.S. PATENT DOCUMENTS

| 15,192 | A | 6/1856 | Peale |
| 2,682,057 | A | 6/1954 | Lord |
| 2,701,559 | A | 2/1955 | Cooper |
| 2,832,078 | A | 4/1958 | Williams |
| 3,029,819 | A | 4/1962 | Starks |
| 3,099,016 | A | 7/1963 | Lowell |
| 3,113,586 | A | 12/1963 | Edmark |
| 3,130,418 | A | 4/1964 | Head et al. |
| 3,143,742 | A | 8/1964 | Cromie |

(Continued)

FOREIGN PATENT DOCUMENTS

| AU | 2002329324 B2 | 7/2007 |
| CN | 1338951 A | 3/2002 |

(Continued)

OTHER PUBLICATIONS

US 8,062,356 B2, 11/2011, Salahieh et al. (withdrawn)

(Continued)

*Primary Examiner* — Suba Ganesan
(74) *Attorney, Agent, or Firm* — Seager, Tufte & Wickhem LLP

(57) ABSTRACT

A medical implant may include an expandable anchor member having a lumen extending through the expandable anchor member from an inflow end to an outflow end; a plurality of valve leaflets disposed within the lumen extending through the expandable anchor member; a seal member disposed adjacent an exterior of the expandable anchor member; and a porous material extending from the seal member to the plurality of valve leaflets.

20 Claims, 10 Drawing Sheets

(56) References Cited

U.S. PATENT DOCUMENTS

| | | |
|---|---|---|
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz et al. |
| 3,409,013 A | 11/1968 | Henry |
| 3,445,916 A | 5/1969 | Schulte |
| 3,503,079 A | 3/1970 | Smith |
| 3,540,431 A | 11/1970 | Mobin-Uddin |
| 3,546,711 A | 12/1970 | Bokros |
| 3,548,417 A | 12/1970 | Kischer et al. |
| 3,551,913 A | 1/1971 | Shiley et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,725,961 A | 4/1973 | Magovem et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,473,423 A | 9/1984 | Kolff |
| 4,484,365 A | 11/1984 | Murguet et al. |
| 4,484,579 A | 11/1984 | Meno et al. |
| 4,490,859 A | 1/1985 | Black et al. |
| 4,501,030 A | 2/1985 | Lane |
| 4,510,628 A | 4/1985 | Kolff |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,739,759 A | 4/1988 | Rexroth et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,326,372 A | 7/1994 | Mhatre et al. |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,739 A | 6/1995 | Jessen |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |
| 5,476,506 A | 12/1995 | Lunn |
| 5,476,510 A | 12/1995 | Eberhardt et al. |

(56) References Cited

U.S. PATENT DOCUMENTS

| | | |
|---|---|---|
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |
| 5,507,767 A | 4/1996 | Maeda et al. |
| 5,522,881 A | 6/1996 | Lentz |
| 5,534,007 A | 7/1996 | Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Faheri et al. |
| 5,607,464 A | 3/1997 | Frescony et al. |
| 5,609,626 A | 3/1997 | Quijano et al. |
| 5,628,784 A | 5/1997 | Strecker |
| 5,645,559 A | 7/1997 | Hachtman et al. |
| 5,653,745 A | 8/1997 | Trescony et al. |
| 5,662,671 A | 9/1997 | Barbut et al. |
| 5,667,523 A | 9/1997 | Bynon et al. |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson et al. |
| 6,045,576 A | 4/2000 | Starr et al. |
| 6,051,014 A | 4/2000 | Jang |
| 6,059,827 A | 5/2000 | Fenton |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Fsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,911 B1 | 3/2001 | Milo |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,254,636 B1 | 7/2001 | Peredo |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,350,282 B1 | 2/2002 | Eberhardt |
| 6,352,554 B2 | 3/2002 | Paulis |

(56) References Cited

U.S. PATENT DOCUMENTS

| | | |
|---|---|---|
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |
| 6,527,800 B1 | 3/2003 | McGuckin et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,558,417 B2 | 5/2003 | Peredo |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,951,573 B1 | 10/2005 | Dilling |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |

(56) References Cited

U.S. PATENT DOCUMENTS

| | | |
|---|---|---|
| 7,147,663 B1 | 12/2006 | Berg et al. |
| 7,166,097 B2 | 1/2007 | Barbut |
| 7,172,625 B2 | 2/2007 | Shu et al. |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,175,659 B2 | 2/2007 | Hill et al. |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,318,278 B2 | 1/2008 | Zhang et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Tobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,524,331 B2 | 4/2009 | Birdsall |
| 7,530,995 B2 | 5/2009 | Quijano et al. |
| 7,544,206 B2 | 6/2009 | Cohn |
| 7,575,594 B2 | 8/2009 | Sieracki |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,670,370 B2 | 3/2010 | Hill et al. |
| 7,674,282 B2 | 3/2010 | Wu et al. |
| 7,712,606 B2 | 5/2010 | Salahieh et al. |
| 7,717,955 B2 | 5/2010 | Lane et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,819,915 B2 | 10/2010 | Stobie et al. |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 7,993,394 B2 | 8/2011 | Hariton et al. |
| 8,012,135 B2 | 9/2011 | Dann et al. |
| 8,029,564 B2 | 10/2011 | Johnson et al. |
| 8,048,153 B2 | 11/2011 | Salahieh et al. |
| 8,052,749 B2 | 11/2011 | Salahieh et al. |
| 8,075,611 B2 | 12/2011 | Millwee et al. |
| 8,136,659 B2 | 3/2012 | Salahieh et al. |
| 8,157,853 B2 | 4/2012 | Laske et al. |
| 8,163,014 B2 | 4/2012 | Lane et al. |
| 8,172,892 B2 | 5/2012 | Chuter et al. |
| 8,172,896 B2 | 5/2012 | McNamara et al. |
| 8,182,528 B2 | 5/2012 | Salahieh et al. |
| 8,192,351 B2 | 6/2012 | Fishier et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,737 B2 | 4/2014 | Gainor |
| 8,696,743 B2 | 4/2014 | Holecek et al. |
| 8,778,020 B2 | 7/2014 | Gregg et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,129 B2 | 10/2015 | Valdez et al. |
| 9,168,131 B2 | 10/2015 | Yohanan et al. |
| 9,675,451 B2 | 6/2017 | Garde et al. |
| 9,861,477 B2 | 1/2018 | Backus et al. |
| 9,895,225 B2 | 2/2018 | Rolando et al. |
| 9,974,649 B2 | 5/2018 | Racchini et al. |
| 10,080,652 B2 | 9/2018 | Backus et al. |
| 10,136,991 B2 | 11/2018 | Backus et al. |
| 10,327,892 B2 | 6/2019 | O'Connor et al. |
| 10,405,974 B2 | 9/2019 | Hayes |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |
| 2002/0058994 A1 | 5/2002 | Hill et al. |
| 2002/0058995 A1 | 5/2002 | Stevens |

(56) References Cited

U.S. PATENT DOCUMENTS

| | | |
|---|---|---|
| 2002/0077696 A1 | 6/2002 | Zadno-Azizi et al. |
| 2002/0077698 A1 | 6/2002 | Peredo |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Fang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0114924 A1 | 6/2003 | Moe |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0176912 A1 | 9/2003 | Chuter et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0195620 A1 | 10/2003 | Huynh et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0015232 A1 | 1/2004 | Shu et al. |
| 2004/0019374 A1 | 1/2004 | Hojeibane et al. |
| 2004/0030381 A1 | 2/2004 | Shu |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225352 A1* | 11/2004 | Osborne ............... A61F 2/2418 623/1.24 |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |

(56) References Cited

U.S. PATENT DOCUMENTS

| | | |
|---|---|---|
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025854 A1 | 2/2006 | Lashinski et al. |
| 2006/0025855 A1 | 2/2006 | Lashinski et al. |
| 2006/0025857 A1 | 2/2006 | Bergheim et al. |
| 2006/0058872 A1 | 3/2006 | Salahieh et al. |
| 2006/0058889 A1* | 3/2006 | Case .................. A61F 2/2418 623/1.24 |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0253191 A1 | 11/2006 | Salahieh et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271172 A1 | 11/2006 | Tehrani |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0018214 A1 | 1/2007 | Ahn et al. |
| 2007/0027535 A1 | 2/2007 | Purdy et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0129795 A1 | 6/2007 | Hill et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0282436 A1 | 12/2007 | Pinchuk |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0033543 A1 | 2/2008 | Gurskis et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0275540 A1 | 11/2008 | Wen |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0216312 A1 | 8/2009 | Straubinger et al. |
| 2009/0222076 A1 | 9/2009 | Figulla et al. |
| 2009/0240320 A1 | 9/2009 | Tuval et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0023120 A1 | 1/2010 | Holecek et al. |
| 2010/0036479 A1 | 2/2010 | Hill et al. |
| 2010/0036484 A1 | 2/2010 | Hariton et al. |
| 2010/0049313 A1 | 2/2010 | Alon et al. |
| 2010/0082089 A1 | 4/2010 | Quadri et al. |
| 2010/0082094 A1 | 4/2010 | Quadri et al. |
| 2010/0094392 A1 | 4/2010 | Nguyen et al. |
| 2010/0094399 A1 | 4/2010 | Dorn et al. |
| 2010/0100176 A1 | 4/2010 | Elizondo et al. |
| 2010/0121434 A1 | 5/2010 | Paul et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0168844 A1 | 7/2010 | Toomes et al. |

(56) References Cited

U.S. PATENT DOCUMENTS

| | | |
|---|---|---|
| 2010/0185275 A1 | 7/2010 | Richter et al. |
| 2010/0191320 A1 | 7/2010 | Straubinger et al. |
| 2010/0191326 A1 | 7/2010 | Alkhatib |
| 2010/0191327 A1 | 7/2010 | Lane et al. |
| 2010/0219092 A1 | 9/2010 | Salahieh et al. |
| 2010/0249894 A1 | 9/2010 | Oba et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256752 A1 | 10/2010 | Forster et al. |
| 2010/0262231 A1 | 10/2010 | Tuval et al. |
| 2010/0280495 A1 | 11/2010 | Paul et al. |
| 2010/0298931 A1 | 11/2010 | Quadri et al. |
| 2011/0000073 A1 | 1/2011 | O'Fallon et al. |
| 2011/0098802 A1 | 4/2011 | Braido et al. |
| 2011/0125258 A1 | 5/2011 | Centola |
| 2011/0166648 A1 | 7/2011 | Robin et al. |
| 2011/0172765 A1 | 7/2011 | Nguyen et al. |
| 2011/0213460 A1 | 9/2011 | Lashinski et al. |
| 2011/0218619 A1 | 9/2011 | Benichou et al. |
| 2011/0224781 A1 | 9/2011 | White |
| 2011/0230956 A1 | 9/2011 | White |
| 2011/0245918 A1 | 10/2011 | White |
| 2011/0257735 A1 | 10/2011 | Salahieh et al. |
| 2011/0264196 A1 | 10/2011 | Savage et al. |
| 2011/0276128 A1 | 11/2011 | Cao et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2011/0319991 A1 | 12/2011 | Hariton et al. |
| 2012/0016469 A1 | 1/2012 | Salahieh et al. |
| 2012/0016471 A1 | 1/2012 | Salahieh et al. |
| 2012/0022629 A1 | 1/2012 | Perera et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059454 A1 | 3/2012 | Millwee et al. |
| 2012/0078356 A1 | 3/2012 | Fish et al. |
| 2012/0078357 A1 | 3/2012 | Conklin |
| 2012/0089224 A1 | 4/2012 | Haug et al. |
| 2012/0095549 A1 | 4/2012 | Forster et al. |
| 2012/0101567 A1 | 4/2012 | Jansen |
| 2012/0123529 A1 | 5/2012 | Levi et al. |
| 2012/0132547 A1 | 5/2012 | Salahieh et al. |
| 2012/0136432 A1 | 5/2012 | Forster et al. |
| 2012/0143316 A1 | 6/2012 | Seguin et al. |
| 2012/0179244 A1 | 7/2012 | Schankereli et al. |
| 2012/0185039 A1 | 7/2012 | Tuval et al. |
| 2012/0197379 A1 | 8/2012 | Laske et al. |
| 2012/0226348 A1 | 9/2012 | Lane et al. |
| 2012/0232459 A1 | 9/2012 | Dann et al. |
| 2012/0245706 A1 | 9/2012 | Alavi et al. |
| 2012/0259409 A1 | 10/2012 | Nguyen et al. |
| 2012/0277850 A1 | 11/2012 | Bertini |
| 2012/0303113 A1 | 11/2012 | Benichou et al. |
| 2012/0303116 A1 | 11/2012 | Gorman et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0046373 A1 | 2/2013 | Cartledge et al. |
| 2013/0079867 A1 | 3/2013 | Hoffman et al. |
| 2013/0079869 A1 | 3/2013 | Straubinger et al. |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0123796 A1 | 5/2013 | Sutton et al. |
| 2013/0138207 A1 | 5/2013 | Quadri et al. |
| 2013/0158656 A1 | 6/2013 | Sutton et al. |
| 2013/0184813 A1 | 7/2013 | Quadri et al. |
| 2013/0190865 A1 | 7/2013 | Anderson |
| 2013/0304199 A1 | 11/2013 | Sutton et al. |
| 2014/0000112 A1 | 1/2014 | Braido et al. |
| 2014/0005772 A1 | 1/2014 | Edelman et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0172077 A1 | 6/2014 | Bruchman et al. |
| 2014/0243966 A1 | 8/2014 | Garde et al. |
| 2014/0243967 A1 | 8/2014 | Salahieh et al. |
| 2014/0277417 A1 | 9/2014 | Schraut et al. |
| 2014/0277423 A1 | 9/2014 | Alkhatib et al. |
| 2014/0350668 A1 | 11/2014 | Delaloye et al. |
| 2015/0005863 A1 | 1/2015 | Para |
| 2015/0012085 A1 | 1/2015 | Salahieh et al. |
| 2015/0073540 A1 | 3/2015 | Salahieh et al. |
| 2015/0073541 A1 | 3/2015 | Salahieh et al. |
| 2015/0127094 A1 | 5/2015 | Salahieh et al. |
| 2015/0142104 A1 | 5/2015 | Braido |
| 2015/0157455 A1 | 6/2015 | Hoang et al. |
| 2015/0320552 A1 | 11/2015 | Letac et al. |
| 2015/0320556 A1 | 11/2015 | Levi et al. |
| 2015/0327995 A1 | 11/2015 | Morin et al. |
| 2016/0045307 A1 | 2/2016 | Yohanan et al. |
| 2016/0199184 A1 | 7/2016 | Ma et al. |
| 2016/0213467 A1 | 7/2016 | Backus et al. |
| 2016/0220365 A1 | 8/2016 | Backus et al. |
| 2016/0256270 A1 | 9/2016 | Folan et al. |
| 2017/0049566 A1 | 2/2017 | Zeng et al. |
| 2017/0304049 A1 | 10/2017 | Hayes |
| 2017/0333183 A1 | 11/2017 | Backus |
| 2018/0353293 A1* | 12/2018 | Colavito ............... A61F 2/2412 |
| 2019/0110893 A1* | 4/2019 | Haarer ................ A61F 2/2436 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 0937439 B1 | 9/2003 |
| EP | 1340473 A2 | 9/2003 |
| EP | 1356793 A3 | 3/2004 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1469797 A1 | 10/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1589902 A1 | 11/2005 |
| EP | 1600121 A1 | 11/2005 |

(56) References Cited

FOREIGN PATENT DOCUMENTS

| | | |
|---|---|---|
| EP | 1156757 B1 | 12/2005 |
| EP | 1616531 A2 | 1/2006 |
| EP | 1605871 B1 | 7/2008 |
| EP | 2119417 A2 | 11/2009 |
| EP | 2749254 B1 | 6/2015 |
| EP | 2898858 A1 | 7/2015 |
| EP | 2926766 A1 | 10/2015 |
| FR | 2788217 A1 | 7/2000 |
| GB | 2056023 A | 3/1981 |
| GB | 2398245 A | 8/2004 |
| JP | 2006333940 A | 12/2006 |
| JP | 2007516055 A | 6/2007 |
| JP | 2010540079 A | 12/2010 |
| JP | 2014530724 A | 11/2014 |
| JP | 2014531292 A | 11/2014 |
| JP | 2015518775 A | 7/2015 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106958 A1 | 2/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023185 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2005062980 A3 | 5/2006 |
| WO | 2006127412 A1 | 11/2006 |
| WO | 2006138391 A2 | 12/2006 |
| WO | 2007033093 A2 | 3/2007 |
| WO | 2007035471 A2 | 3/2007 |
| WO | 2005102015 A3 | 4/2007 |
| WO | 2007044285 A2 | 4/2007 |
| WO | 2007058847 A2 | 5/2007 |
| WO | 2007092354 A2 | 8/2007 |
| WO | 2007097983 A2 | 8/2007 |
| WO | 2007053243 A2 | 9/2007 |
| WO | 2009042196 A2 | 4/2009 |
| WO | 2010017537 A2 | 2/2010 |
| WO | 2010042950 A2 | 4/2010 |
| WO | 2010098857 A1 | 9/2010 |
| WO | 2012116368 A2 | 8/2012 |
| WO | 2012162228 A1 | 11/2012 |
| WO | 2013009975 A1 | 1/2013 |
| WO | 2013012801 A2 | 1/2013 |
| WO | 2013028387 A2 | 2/2013 |
| WO | 2013070896 A1 | 5/2013 |
| WO | 2013074671 A1 | 5/2013 |
| WO | 2013096545 A1 | 6/2013 |
| WO | 2013184895 A1 | 12/2013 |
| WO | 2014008207 A1 | 1/2014 |
| WO | 2014140230 A1 | 9/2014 |
| WO | 2014203106 A1 | 12/2014 |
| WO | 2015085218 A1 | 6/2015 |
| WO | 2016126511 A2 | 8/2016 |
| WO | 2016126524 A1 | 8/2016 |
| WO | 2017027289 A1 | 2/2017 |

(56) References Cited

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Knudsen et al., "Catheter-implanted prosthetic heart valves." Int'l J. of Art. Organs, 16(5): 253-262, May 1993.
Kort et al, "Minimally Invasive Aortic Valve Replacement: Echocardiographic and Clinical Results "Am Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "Mycobacterium Chelonei Infection of Porcine Heart Valves." The New England Journal of Medicine, Washington DC, 297(12), Sep. 22, 1977.
Love et al., "The Autogenous Tissue Heart Valve: Current Status." Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48:533-4 (1989).
Maraj et al., Evaluation of Hemolysis in Patients with Prosthetic Heart Valves, Clin. Cardiol. 21, 387-392 (1998).
McKay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170 1033-1037(1989).
Moazami et al., "Transluminal Aortic Valve Placement: A Feasibility Study With a Newly Designed Collapsiable Aortic Valve," ASAIO J. vol. 42:5, pp. M383-M385 (Sep./Oct. 1996).
Moulopoulos et al., "Catheter-Mounted Aortic Valves." Annals of Thoracic Surg., 11 (5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vase. Surg., 5 (6):491-9 (1991).
Pavcnik et al., "Percutaneous Bioprosthetic Venous Valve: A Long-term Study in Sheep." J. of Vascular Surg., 35(3): 598-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. 4/99.
U.S. Appl. No. 60/553,945 to White.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radiol. 15: 319-327 (1992).
Schurink et al.,. "Stent Attachment Site-related Endoleakage after Stent Graft Treatment: An in vitro study of the affects of graft size, stent type, and atherosclerotic wall changes" J. Vasc. Surg., 30(4):658-67 (Oct. 1999).
Deminars in Interventaional Cardiology, ed. P.W. Surruys, vol. 5 (200).
Sochman et al., "Percutaneous Transcatheter Aortic Disc Valve Prosthesis Implantation: A Feasibility Study." Cardiovasc. Intervent Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft The Australasian Experience " J. Endovasc. Ther. 8:457-464 (2001).
Thompson et al., "Endoluminal stent grafting of the thoracic aorta: Initial experience with the Gore Excluder," Journal of Vascular Surgery, 1163-70 (Jun. 2002).
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. Feb. 9-17, 2004.
Supplemental Search Report from EP Patent Office, EP Application No. 04815634.3, dated Aug. 19, 2011.
Supplemental Search Report from EP Patent Office, EP Application No. 05758878.2, dated Oct. 24, 2011.
Textbook of Interventional Cardiology, 2d Ed., Chapter 75: Percutaneous Expandable Prosthetic Valves (1994).
Stassano, "Mid-term Results of the Valve on Valve Technique for Bioprosthetic failure." European journal of Ccardiothoracic Surgery:vol. 18, 453-457, Oct. 2000.
Topol, "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).
USPTO Case IPR2016-___, U.S. Pat. No. 8,992,608 "Petition for Interpartes Review of U.S. Pat. No. 8,992,608" Oct. 12, 2016.
USPTO Case IPR 2017-0006, U.S. Pat. No. 8,992,608 B2, "Final Written Decision" dated Mar. 23, 2018.
Fluency Vascular Stent Graft Instructions for Use (2003).
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.

(56) References Cited

OTHER PUBLICATIONS

Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502 Technical Design Report. Northeastern University, pp. 1-93, Nov. 5, 2007.
Bailey, "Percutaneous Expandable Prosthetic Valves, Textbook of Interventional Cardiology." vol. 2,2d ed. Eric J. Topol, W.B. Saunders Co. (1994).
Blum et al., "Endoluminal Stent-Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S4 17-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044 1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practive (2000)—EVT Endograft and Talent Endoprosthesis.
Dotter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference Sep. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).
Carpentier-Edwards PERIMOUNT Bioprosthesis (2003).
International Search Report and Written Opinion dated Oct. 22, 2018 for International Application No. PCT/US2018/044318.
Invite to Pay Additional Fees and, where Applicable, Protest Fee, dated Nov. 14, 2016 for International Application No. PCT/US2016/045335.
International Search Report and Written Opinion dated Feb. 2, 2017 for International Application No. PCT/US2016/045323.
International Search Report and Written Opinion dated Aug. 16, 2017 for International Application No. PCT/US2017/033160.
International Search Report and Written Opinion dated Apr. 21, 2016 for International Application No. PCT/US2016/014878.
International Preliminary Report on Patentability and Written Opinion dated Aug. 10, 2017 for International Application No. PCT/US2016/014878.
International Search Report and Written Opinion dated Jul. 17, 2017 for International Application No. PCT/US2017/029552.

(56) References Cited

OTHER PUBLICATIONS

International Search Report and Written Opinion dated Jul. 12, 2016 for International Application PCT/US2016/014401.

* cited by examiner

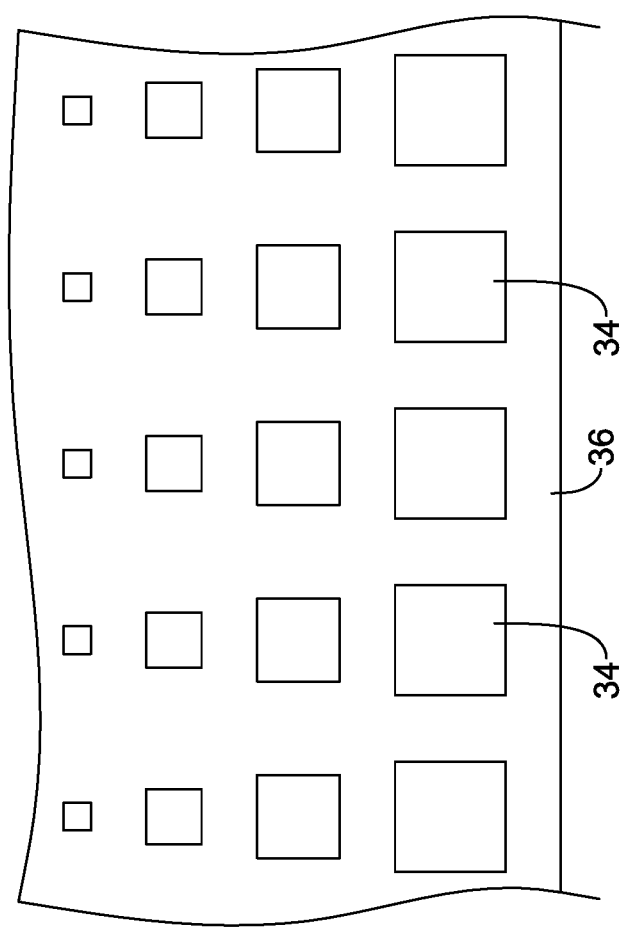

REPLACEMENT HEART VALVE WITH IMPROVED CUSP WASHOUT AND REDUCED LOADING

CROSS-REFERENCE TO RELATED APPLICATIONS

This application claims the benefit of priority of U.S. Provisional Application No. 62/846,018 filed May 10, 2019, the entire disclosure of which is hereby incorporated by reference.

TECHNICAL FIELD

The present disclosure pertains to medical devices, and methods for manufacturing and/or using medical devices. More particularly, the present disclosure pertains to an improved design for a medical device and/or a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a medical implant may comprise an expandable anchor member having a lumen extending through the expandable anchor member from an inflow end to an outflow end; a plurality of valve leaflets disposed within the lumen extending through the expandable anchor member; a seal member disposed adjacent an exterior of the expandable anchor member; and a porous material extending from the seal member to the plurality of valve leaflets.

In addition or alternatively, the seal member is disposed outside of the lumen extending through the expandable anchor member.

In addition or alternatively, at least a portion of the porous material is disposed within the lumen extending through the expandable anchor member.

In addition or alternatively, the seal member includes a reinforcing band disposed proximate the inflow end of the expandable anchor member.

In addition or alternatively, the porous material extends from the reinforcing band to the plurality of valve leaflets.

In addition or alternatively, the reinforcing band does not pass through interstices in the expandable anchor member.

In addition or alternatively, the porous material does not pass through interstices in the expandable anchor member.

In addition or alternatively, the porous material includes a polymeric coating.

In addition or alternatively, a medical implant may comprise an expandable anchor member having a lumen extending through the expandable anchor member from an inflow end to an outflow end; a plurality of valve leaflets disposed within the lumen extending is through the expandable anchor member; a seal member disposed adjacent an exterior of the expandable anchor member; and a fabric material extending from the seal member to the plurality of valve leaflets, the fabric material having a plurality of holes therethrough permitting fluid to flow between an inflow side of the plurality of valve leaflets and an outflow side of the plurality of valve leaflets without passing through the plurality of valve leaflets.

In addition or alternatively, at least one seal stitch secures the seal member to the fabric material.

In addition or alternatively, the at least one seal stitch includes at least one whip stitch.

In addition or alternatively, at least one leaflet stitch secures the fabric material to the plurality of valve leaflets.

In addition or alternatively, the at least one leaflet stitch includes at least one whip stitch.

In addition or alternatively, the at least one leaflet stitch includes a running stitch.

In addition or alternatively, the at least one leaflet stitch includes a double running stitch.

In addition or alternatively, a medical implant may comprise an expandable anchor member having a lumen extending through the expandable anchor member from an inflow end to an outflow end; a plurality of valve leaflets disposed within the lumen extending through the expandable anchor member; and a seal member disposed adjacent an exterior of the expandable anchor member and attached to the plurality of valve leaflets at the inflow end of the expandable anchor member. The plurality of valve leaflets may each include a thinned region disposed proximate the inflow end of the expandable anchor member.

In addition or alternatively, the thinned region includes a plurality of holes extending through the thinned region permitting fluid to flow between an inflow side of the plurality of valve leaflets and an outflow side of the plurality of valve leaflets without passing through a lumen defined by free edges of the plurality of leaflets.

In addition or alternatively, the plurality of holes has a variable size.

In addition or alternatively, the plurality of holes decreases in size in a direction is from the inflow end of the expandable anchor member toward the outflow end of the expandable anchor member.

In addition or alternatively, the thinned region does not pass through interstices in the expandable anchor member.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 9 illustrates selected aspects of the example medical implant.

Figure 1:
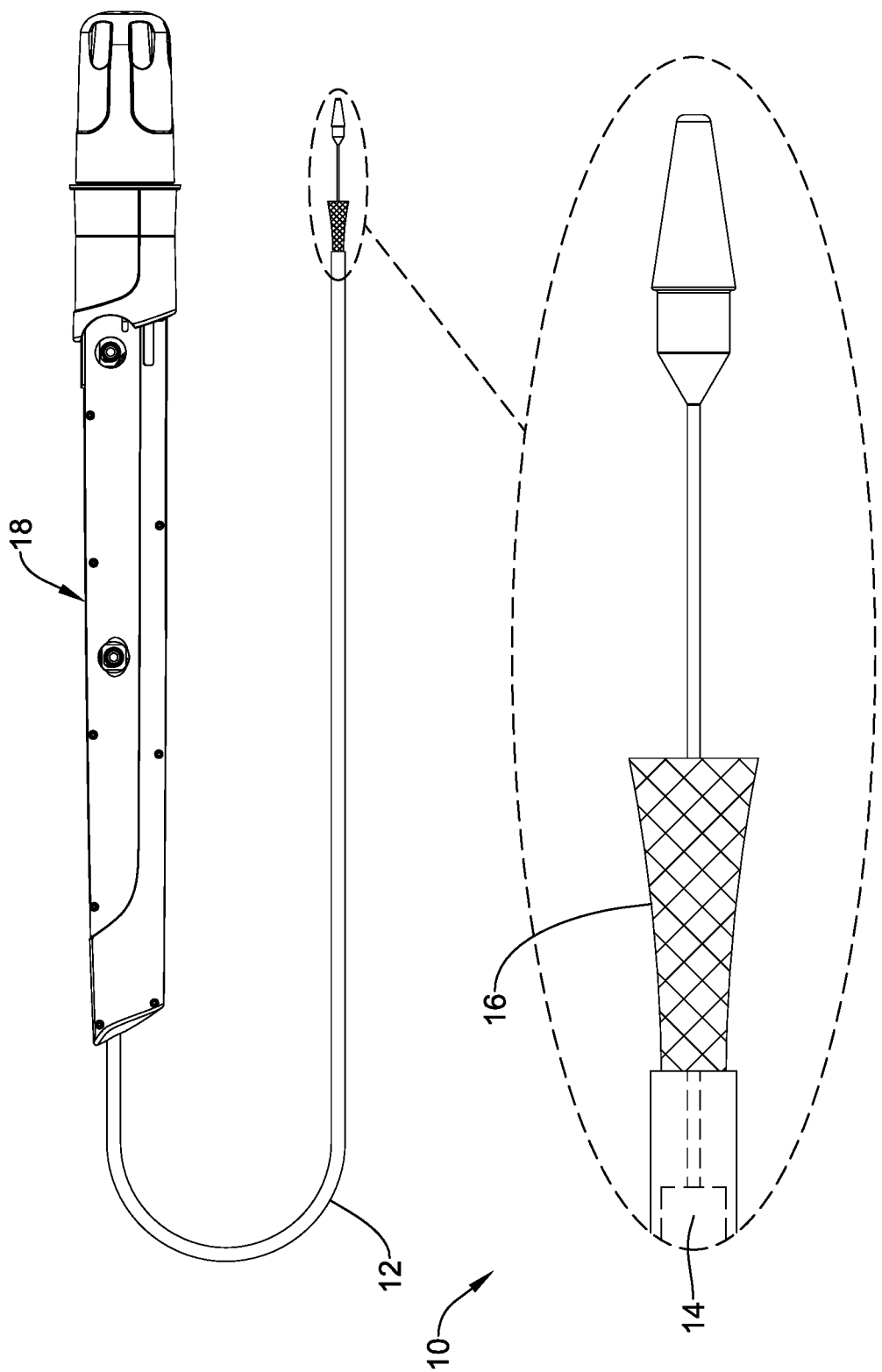
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, is the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered is a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to a serious health condition and/or death if not dealt with properly. Treatment of defective heart valves poses other challenges in that the treatment often requires the repair or outright replacement of the defective heart valve. Such therapies may be highly invasive to the patient. Disclosed herein is a medical device system that may be used for delivering a medical implant to a portion of the cardiovascular system in order to diagnose, treat, and/or repair the system. At least some of the medical implants and/or systems disclosed herein may be used to deliver and implant a replacement heart valve implant (e.g., a replacement aortic valve, replacement mitral valve, etc.). In addition, the medical device system may deliver the replacement heart valve implant percutaneously and, thus, may be much less invasive to the patient. The device and/or system disclosed herein may also provide other desirable features and/or benefits as described below.

The figures illustrate selected components and/or arrangements of a medical device system 10. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

The medical device system 10, as seen in FIG. 1 for example, may generally be described as a catheter system that includes a delivery system having an outer sheath 12 for a medical implant 16 (i.e., a replacement heart valve implant, for example, which term may be used interchangeably with the term "medical implant" herein) which may be coupled to the delivery system and disposed within a lumen of the outer sheath 12 during delivery of the medical implant 16. In some embodiments, the delivery system may include an inner catheter 14 extending at least partially through the outer sheath 12 (partially seen in phantom in FIG. 1). In some embodiments, the medical implant 16 may be coupled to the inner catheter 14 and disposed within the lumen of the outer sheath 12 during delivery of the medical implant 16. In some embodiments, a handle 18 may be disposed and/or attached at a proximal end of the delivery system, as seen in FIG. 1, and may include one or more actuation means associated therewith. In some embodiments, the handle 18 may have an outer shell and an interior space. In some embodiments, the handle 18 may have a control knob rotatable relative to the outer shell of the handle 18. In some embodiments, the handle 18 and/or the control knob may be configured to manipulate the position of the outer sheath 12 relative to the inner catheter 14 and/or the medical implant 16, and/or to aid in the deployment of the medical implant 16. In some embodiments, the medical device system 10 may include a nose cone disposed at a distal end of a guidewire extension tube, wherein the guidewire extension tube may extend distally from the inner catheter 14. In at least some embodiments, the nose cone may be designed to have an atraumatic shape. In some embodiments, the nose cone may include a ridge or ledge that is configured to abut a distal tip of the outer sheath 12 during delivery of the medical implant 16. Some suitable but non-limiting materials for the medical device system 10, the outer sheath 12, the inner catheter 14, the handle 18, the control knob, and/or components or elements thereof, for example metallic materials and/or polymeric materials, are described below.

In use, the medical device system 10 may be advanced percutaneously through the is vasculature to a position adjacent to an area of interest or a target location. For example, the medical device system 10 may be advanced through the vasculature and across the aortic arch to a position adjacent to a defective aortic valve. Alternative approaches to treat a defective aortic valve and/or other heart valve(s) are also contemplated with the medical device system 10. During delivery, the medical implant 16 may be generally disposed in an elongated and low profile "delivery" configuration within the outer sheath 12 coupled to and/or distal of the inner catheter 14, as seen in FIG. 1, for example. Once positioned, the outer sheath 12 may be retracted relative to the inner catheter 14, which may be held stationary by the handle 18, and/or the medical implant 16 to expose the medical implant 16. The medical implant 16 may be actuated using the handle 18 and/or the control knob in order to translate the medical implant 16 into a generally expanded and larger profile "deployed" configuration (e.g., expanded as in FIG. 2, but still coupled to the inner catheter 14) suitable for implantation within the anatomy. When the medical implant 16 is suitably deployed within the anatomy, the medical implant 16 may be released and/or detached from the medical device system 10, the delivery system can be removed from the vasculature, leaving the medical implant 16 in place in a "released" configuration (e.g., FIG. 2) to function as, for example, a suitable replacement for the native aortic valve. In at least some interventions, the medical implant 16 may be deployed within the native valve (e.g., the native valve is left in place and not excised). Alternatively, the native valve may be removed (such as through valvuloplasty, for example) and the medical implant 16 may be deployed in its place as a replacement.

In at least some embodiments, the medical implant 16 may be disposed in an "everted" configuration or a partially-everted configuration while disposed within the lumen of the outer sheath 12 and/or immediately upon exposure after retracting the outer sheath 12. In some embodiments, the medical implant 16 may be everted in the "delivery" configuration. The "everted" configuration may involve at least a portion of the valve leaflets (discussed below) of the medical implant 16 being disposed outside of the expandable anchor member (discussed below) of the medical implant 16 during delivery, thereby permitting a smaller radial profile of the medical implant 16 and the use of a smaller overall profile of the outer sheath 12 and/or the medical device system 10. In some embodiments, the "delivery" configuration and the "everted" configuration may be is substantially similar and/or may be used interchangeably herein.

In some embodiments, the inner catheter 14 may be a tubular structure having one or more lumens extending therethrough. For example, in some embodiments, the inner catheter 14 may include one or more of a first lumen, a second lumen, a third lumen, and a fourth lumen. Other configurations are also contemplated. In some embodiments, the one or more lumens may extend along an entire length of the inner catheter 14. Other embodiments are contemplated, however, wherein one or more of the one or more lumens extend along only a portion of the length of the inner catheter 14. In some embodiments, a coupler assembly may be attached to the inner catheter 14 at and/or proximate a distal end of the inner catheter 14. In some embodiments, the coupler assembly may releasably couple the medical implant 16 to the inner catheter 14.

In some embodiments, the medical device system 10 may include at least one actuator element (not shown) releasably connecting the medical implant to the handle 18. For example, the at least one actuator element may extend from the handle 18 to the medical implant 16, the medical implant being disposed at a distal end of the lumen of the outer sheath 12. The at least one actuator element may extend distally from the inner catheter 14 to the medical implant 16. In some embodiments, the at least one actuator element may be slidably disposed within and/or may extend slidably through the inner catheter 14. For example, the at least one actuator element may be slidably disposed within one or more of the lumens of the inner catheter 14, and may be used to actuate (i.e., translate axially or longitudinally, and/or expand) the medical implant 16 between the "delivery" configuration, the "deployed" configuration, and/or the "released" configuration. In some embodiments, the at least one actuator element may include a plurality of actuator elements, two actuator elements, three actuator elements, four actuator elements, or another suitable or desired number of actuator elements.

Figure 2:
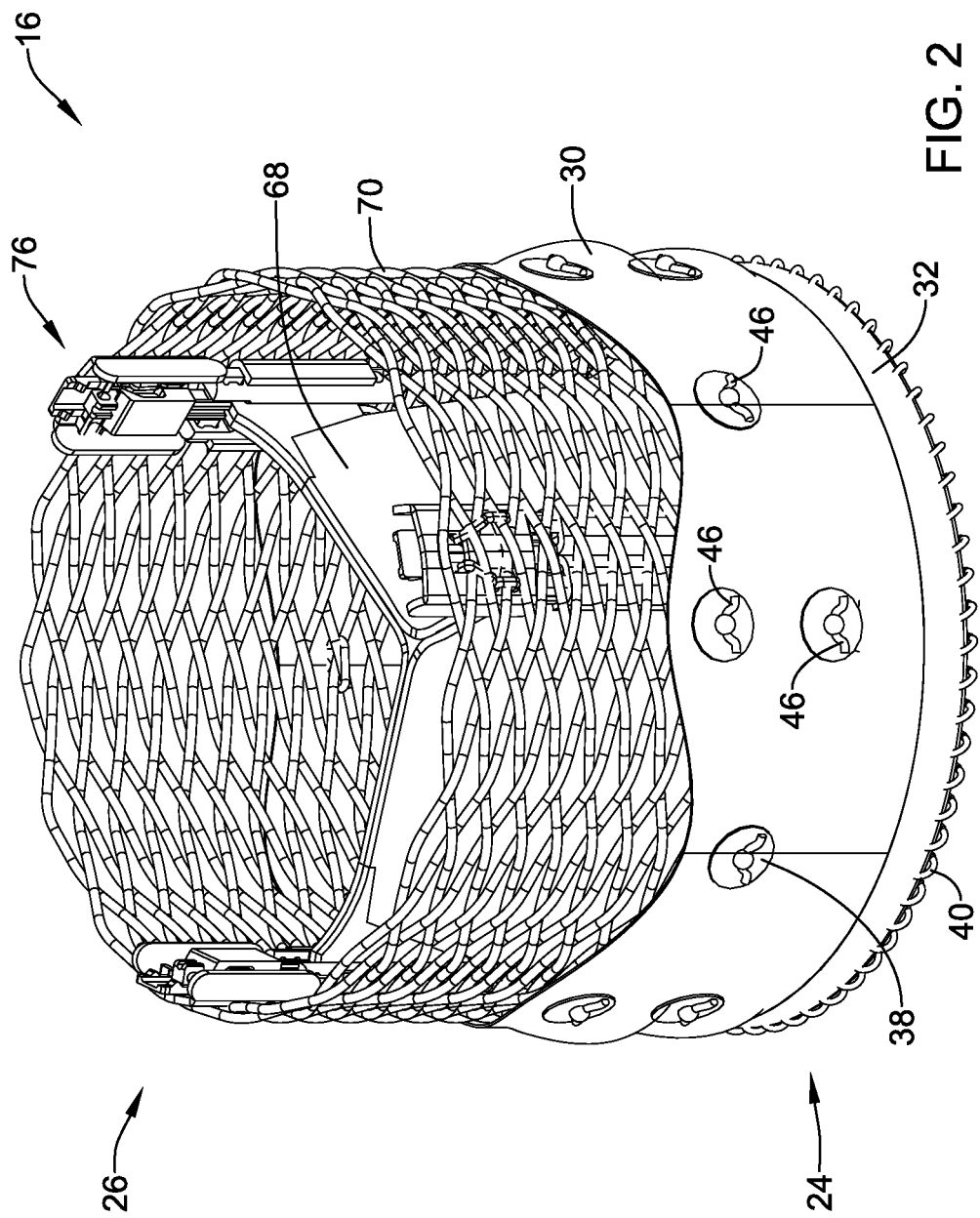
FIG. 2 illustrates an example medical implant associated with the example medical device system.

For the purpose of discussion only, the medical device system 10 and/or the medical implant 16 of FIG. 2 may be configured to use three actuator elements (not shown). In use, a proximal end of each actuator element may be connected to the handle 18, and/or manipulated or otherwise actuated by a user using the handle 18 and/or the control knob, to reversibly shift the medical implant 16 from a "delivery" configuration to a "deployed" configuration, and to later shift the medical implant from the "deployed" configuration to a "released" configuration. During the release process for the medical implant 16, (e.g., as the medical implant 16 is actuated from the "delivery" configuration to the "deployed" configuration to the "released" configuration), the at least one actuator element may be retracted, withdrawn, and/or translated proximally relative to the inner catheter 14 and/or the medical implant 16. Some suitable but non-limiting materials for the actuator element, for example metallic materials or polymeric materials, are described below.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element", "the leaflets", "the lumen", or other features may be equally referred to all instances and quantities beyond one of said feature. As such, it will be understood that the following discussion may apply equally to any and/or all of the components for which there are more than one within the medical implant 16 (i.e., the at least one actuator element, the plurality of leaflets, etc.) and/or the medical device system 10, unless explicitly stated to the contrary. Additionally, not all instances of some elements or features may be shown in each figure for clarity.

FIG. 2 illustrates some selected components of the medical implant 16. For example, here it can be seen that the medical implant 16 may include a plurality of valve leaflets 68 (e.g., bovine pericardial, polymeric, etc.) which may be secured to an expandable anchor member 70 that is reversibly actuatable between an elongated "delivery" configuration and an expanded "deployed" configuration. In some embodiments, the expandable anchor member 70 may form a tubular structure defining a central longitudinal axis and a lumen extending through the expandable anchor member 70 along, parallel to, coaxial with, and/or coincident with the central longitudinal axis from an inflow end 24 of the expandable anchor member 70 to an outflow end 26 of the expandable anchor member 70. In some embodiments, the expandable anchor member 70 may be and/or include an expandable stent having a plurality of struts. In some embodiments, the expandable anchor member 70 may be and/or include a braid formed from one or more filaments (e.g., a single filament, two filaments, etc.). The expandable anchor member 70 may include a plurality of interstices (e.g., openings) disposed in the is expandable anchor member 70. The plurality of interstices (e.g., openings) may pass from an interior or the expandable anchor member 70 to an exterior of the expandable anchor member 70 between adjacent struts and/or filaments. In some embodiments, the expandable anchor member 70 may be self-expanding. In some embodiments, the expandable anchor member 70 may be expanded via mechanical means, using a balloon, or other suitable methods of expansion. Other configurations are also contemplated. Some suitable but non-limiting materials for the expandable anchor member 70, for example metallic materials, polymeric materials, shape memory materials, etc., are described below.

In some embodiments, the medical implant 16 may include a plurality of locking elements 76 attached to the expandable anchor member 70, the plurality of locking elements 76 being configured to lock the expandable anchor member 70 in the "deployed" and/or "released" configuration(s). In some embodiments, the at least one actuator element may be configured to actuate the expandable anchor member 70 and/or the medical implant 16 between the "delivery" configuration and the "deployed" configuration and/or the "released" configuration.

In some embodiments, the plurality of locking elements 76 may each comprise an axially movable post member, for example at the commissure portions of the valve leaflets 68 (the post member may sometimes be referred to as a portion of a commissure post, which may serve to secure the valve leaflets 68, or the post member may be connected and/or attached to a commissure post), and a buckle member or other receiving element configured to slidably receive the post member therein to engage with the buckle member and thereafter lock the expandable anchor member 70 and/or the medical implant 16 in the "deployed" and/or the "released" configuration(s). In other words, in at least some embodiments, a medical implant 16 may include a plurality of post members and a corresponding plurality of buckle members. Other configurations and correspondences are also contemplated. Some suitable but non-limiting materials for the plurality of locking elements 76, the buckle member, and/or the post member, for example metallic materials or polymeric materials, are described below.

In some embodiments, the plurality of valve leaflets 68 may be secured to the expandable anchor member 70 at, adjacent to, and/or using (at least in part) corresponding post members. In some embodiments, the plurality of valve leaflets 68 may also be secured to the inflow end 24 of the expandable anchor member 70. In some embodiments, the plurality of valve leaflets 68 may be coupled and/or secured (i.e., to the post member, to the expandable anchor member 70, and/or back to themselves) using one or more sutures, threads, wires, filaments, adhesives, bonding agents, or other suitable elements and/or combinations thereof. In some embodiments, the plurality of valve leaflets 68 may be directly attached to the expandable anchor member 70. In some embodiments, the plurality of valve leaflets 68 may not be directly attached to the expandable anchor member 70.

In some embodiments, the post members and/or the commissure posts may be secured and/or attached to the expandable anchor member 70 (e.g., along the interior of the expandable anchor member) with sutures, tethers, adhesives, or other suitable elements. In some embodiments, the commissure post and/or the post member may include one or more holes or other features provided to aid in securing and/or attaching the commissure post and/or the post member to the expandable anchor member 70. Positioned adjacent to (e.g., aligned with) the plurality of post members is a corresponding plurality of buckle members, which may be secured and/or fixedly attached to the expandable anchor member 70 (e.g., along the interior of the expandable anchor member 70) with sutures, adhesives, or other suitable mechanisms. In some embodiments, the post member may be axially translatable relative to the buckle member generally parallel to the central longitudinal axis of the expandable anchor member 70 when the post member is at least partially disposed within and/or engaged with the buckle member.

In some embodiments, one buckle member may be fixedly attached to the expandable anchor member 70 adjacent to each of the post members. Accordingly, in some embodiments, the expandable anchor member 70 may have a total of three buckle members and three post members attached thereto. Similarly, one actuator element may be associated with each post member and buckle member, for a total of three actuator elements in the given example(s). Other embodiments are contemplated where fewer or more buckle members, post members, and/or actuator elements may be utilized.

In some embodiments, a seal member 30 may be circumferentially disposed on, about, and/or adjacent the exterior of the expandable anchor member 70, as seen in FIG. 2 for example, and as the term suggests, may help to seal the exterior of the medical implant 16 and/or the expandable anchor member 70 within and/or against a target site or area of interest upon deployment, thereby preventing leakage around the medical implant 16 and/or the expandable anchor member 70. The seal member 30 may be disposed outside of the lumen extending through the expandable anchor member 70. In some embodiments, the seal member 30 may be coupled and/or secured to the expandable anchor member 70 at one or more locations.

In some embodiments, the seal member 30 may include a plurality of grommets 38.

The plurality of grommets 38 may be attached to, bonded to, and/or at least partially embedded in the seal member 30. The plurality of grommets 38 may act as reinforcement points for attachment of the seal member 30 to the expandable anchor member 70 using a plurality of lashing sutures 46. In some embodiments, the plurality of lashing sutures 46 may extend through the plurality of grommets 38. In some embodiments, the plurality of lashing sutures 46 may attach the seal member 30 to the expandable anchor member 70 at non-consecutive intersections of the struts or filaments.

In some embodiments, the seal member 30 may include one or more layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other suitable polymeric materials are also contemplated, some of which are discussed below.

In some embodiments, the modulus of elasticity may vary and/or be different from layer to layer. In other embodiments, the elongation to break may vary and/or be different from layer to layer. In some embodiments, the seal member 30 may also include a reinforcement, a reinforcing layer, and/or one or more reinforcing members added to the polymeric material prior to curing. The reinforcement, the reinforcing layer, and/or the one or more reinforcing members may comprise a woven or nonwoven fabric and may be positioned within or between the various layers. In some embodiments, the reinforcement, the reinforcing layer, and/or the one or more reinforcing members may be positioned on a radially innermost surface or radially outermost surface of the seal member 30. In some embodiments, the reinforcement, the reinforcing layer, and/or the one or more reinforcing members may be generally aligned. In some embodiments, the reinforcement, the reinforcing layer, and/or the one or more reinforcing members may be randomly oriented and/or disposed on the seal member 30. In some embodiments, at least a portion of the seal member 30 may be formed from a fabric material having a polymeric coating 33. In at least some embodiments, the seal member 30 may be impermeable to fluids and/or blood.

In some embodiments, the seal member 30 may include a reinforcing band 32 coupled to the seal member 30 and/or disposed proximate the inflow end 24 of the expandable anchor member 70. In some embodiments, the reinforcing band 32 may be integrally formed with, incorporated into, adhered to, and/or at least partially embedded within the seal member 30. In some embodiments, the reinforcing band 32 may be formed from a woven or nonwoven fabric material, a textile, or other thin flexible material. In some embodiments, the reinforcing band 32 may be the at least a portion of the seal member 30 formed from the fabric material having the polymeric coating 33. The reinforcing band 32 may provide tear resistance in the vicinity of sutures, filaments, or other attachment elements associated with components or aspects of the medical implant 16. In some embodiments, the reinforcing band 32 may have a longitudinal length measured parallel to the central longitudinal axis of about 1.5 millimeters, about 1.8 millimeters, about 2.0 millimeters, about 2.2 millimeters, about 2.5 millimeters, about 3 millimeters, etc.

In some embodiments, at least one seal stitch 40 may attach the inflow end of the seal member 30 and/or the reinforcing band 32 to the inflow end 24 of the expandable anchor member 70. In some embodiments, the at least one seal stitch 40 may include at least one whip stitch. A whip stitch may sometimes be referred to and/or interchanged with a helical stitch. In some embodiments, the at least one seal stitch 40 may form one or more first helical spirals oriented in a first direction about the inflow end 24 of the expandable anchor member 70.

Figure 3:
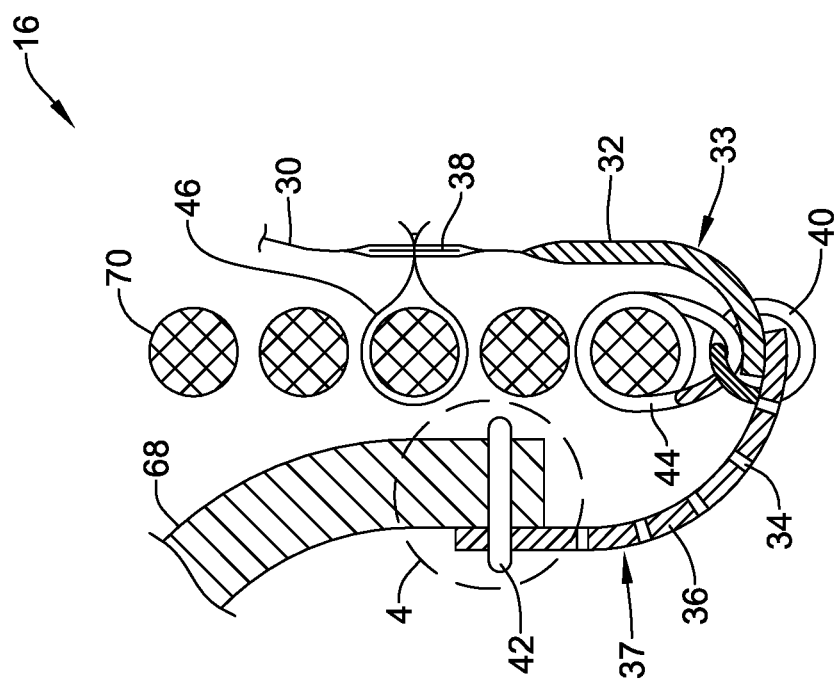
FIG. 3 is a partial section view illustrating aspects of the example medical implant.

In some embodiments, the medical implant 16 may include a porous material 36 extending from the seal member 30 and/or the reinforcing band 32 to the plurality of valve leaflets 68, as seen in FIG. 3 for example. In some embodiments, the porous material 36 may be a fabric material having a plurality of holes 34 therethrough permitting fluid (e.g., blood) to flow between an inflow side of the plurality of valve leaflets 68 and an outflow side of the plurality of valve leaflets 68 without passing through the plurality of valve leaflets 68 and/or without passing through a lumen defined by the free edges of the plurality of valve leaflets 68. For example, the porous material 36 may permit fluid (e.g., blood) to flow through the lumen extending through the expandable anchor member 70 from the inflow side of the plurality of valve leaflets 68 to the outflow side of the plurality of valve leaflets 68, from the outflow side of the plurality of valve leaflets 68 to the inflow side of the plurality of valve leaflets 68, or both, without passing through the plurality of valve leaflets 68 and/or without passing through a lumen defined by the free edges of the plurality of valve leaflets 68. In some embodiments, the porous material 36 may be a blood-permeable material. The blood-permeable material may include a fabric material. In some embodiments, the fabric material of the porous material 36 and/or the blood-permeable material may include a polymeric coating 37 disposed thereon. In some embodiments, the fabric material of the seal member 30 and/or the reinforcing band 32 is the fabric material of the porous material 36 and/or the blood-permeable material. For example, the same fabric material may extend continuously and/or uninterrupted through the seal member 30 and/or the reinforcing band 32 and the porous material 36. In some embodiments, the polymeric coating 33 of the seal member 30 and/or the reinforcing band 32 is the polymeric coating 37 of the porous material 36, the fabric material, and/or the blood-permeable material. For example, the same polymeric coating may be used for both polymeric coating 33 of the seal member 30 and/or the reinforcing band 32 and the polymeric coating 37 of the porous material 36, the fabric material, and/or the blood-permeable material. In some embodiments, the porous material 36 may be and/or may include a form of tissue, such as, but not limited to, bovine pericardial, porcine pericardial, or other suitable tissues (e.g., leaflet material, and the like).

At least a portion of the porous material 36, the blood-permeable material, and/or the fabric material is disposed within the lumen extending through the expandable anchor member 70. In some embodiments, the porous material 36, the fabric material, and/or the blood-permeable material may have about 30% open area, about 35% open area, about 38% open area, about 40% open area, about 45% open area, etc. In some embodiments, the porous material 36, the fabric material, and/or the blood-permeable material may have a longitudinal length measured parallel to the central longitudinal axis of about 3.0 millimeters, about 3.5 millimeters, about 3.8 millimeters, about 4.0 millimeters, about 4.2 millimeters, about 4.5 millimeters, about 5 millimeters, etc.

In some embodiments, the polymeric coating 33 of the seal member 30 and/or the reinforcing band 32 is thicker than the polymeric coating 37 of the porous material 36, the fabric material, and/or the blood-permeable material. For example, the polymeric coating 33 of the seal member 30 and/or the reinforcing band 32 may close, plug, and/or seal off any holes, apertures, pores, and/or openings extending therethrough, while the plurality of holes 34, apertures, pores, and/or openings extending through the porous material 36, the fabric material, and/or the blood-permeable material may be at least partially unobstructed by the polymeric coating 37 thereon. In some embodiments, the polymeric coating 33 of the seal member 30 and/or the reinforcing band 32 may be at least about 30 microns thick, about 40 microns thick, about 50 microns thick, about 55 microns thick, about 60 microns thick, or another suitable thickness. In some embodiments, the polymeric coating 37 of the porous material 36, the fabric material, and/or the blood-permeable material may be less than 10 microns thick, about 5 microns thick, about 3 microns thick, about 2 microns thick, about 1 micron thick, or another suitable thickness.

In some embodiments, the at least one seal stitch 40 may attach the reinforcing band 32 and/or the inflow end of the reinforcing band 32 to an inflow end of the porous material 36 (e.g., the fabric material, etc.) adjacent the inflow end 24 of the expandable anchor member 70. In some embodiments, one or more inflow lashing sutures 44 may secure the at least one seal stitch 40, the inflow end of the porous material 36, the inflow end of the seal member 30, and/or the reinforcing band 32 to the expandable anchor member 70 at, proximate, and/or to the inflow end 24 of the expandable anchor member 70. In at least some embodiments, the one or more inflow lashing sutures 44 may attach the at least one seal stitch 40, the inflow end of the porous material 36, the inflow end of the seal member 30, and/or the reinforcing band 32 to the strut(s), filament(s), and/or intersection(s) thereof of the expandable anchor member 70 disposed and/or positioned closest to the inflow end 24 of the expandable anchor member 70.

In some embodiments, the one or more inflow lashing sutures 44 may directly attach the at least one seal stitch 40 to the inflow end 24 of the expandable anchor member is 70. In some embodiments, the one or more inflow lashing sutures 44 may be interwoven with the at least one seal stitch 40 and/or a plurality of windings of the at least one seal stitch 40 to form a suture lattice. In some embodiments, at least a portion of the one or more inflow lashing sutures 44 may be looped through an interior of one or more of the plurality of windings of the at least one seal stitch 40 to form the suture lattice. In some embodiments, the one or more inflow lashing sutures 44 may form one or more second helical spirals oriented in a second direction about the inflow end 24 of the expandable anchor member 70. In some embodiments, the one or more inflow lashing sutures 44 may form one or more second helical spirals oriented in a second direction about the inflow end 24 of the expandable anchor member 70. In some embodiments, the first direction may be opposite the second direction.

As may be seen in FIG. 3, in at least some embodiments, the seal member 30 and/or the reinforcing band 32 does not pass through interstices in the expandable anchor member 70. In at least some embodiments, the porous material 36, the blood-permeable material, and/or the fabric material does not pass through interstices in the expandable anchor member 70. Instead, the seal member 30, the reinforcing band 32, the porous material 36, the blood-permeable material, and/or the fabric material may extend past and/or around the inflow end 24 of the expandable anchor member 70.

Figure 4A:
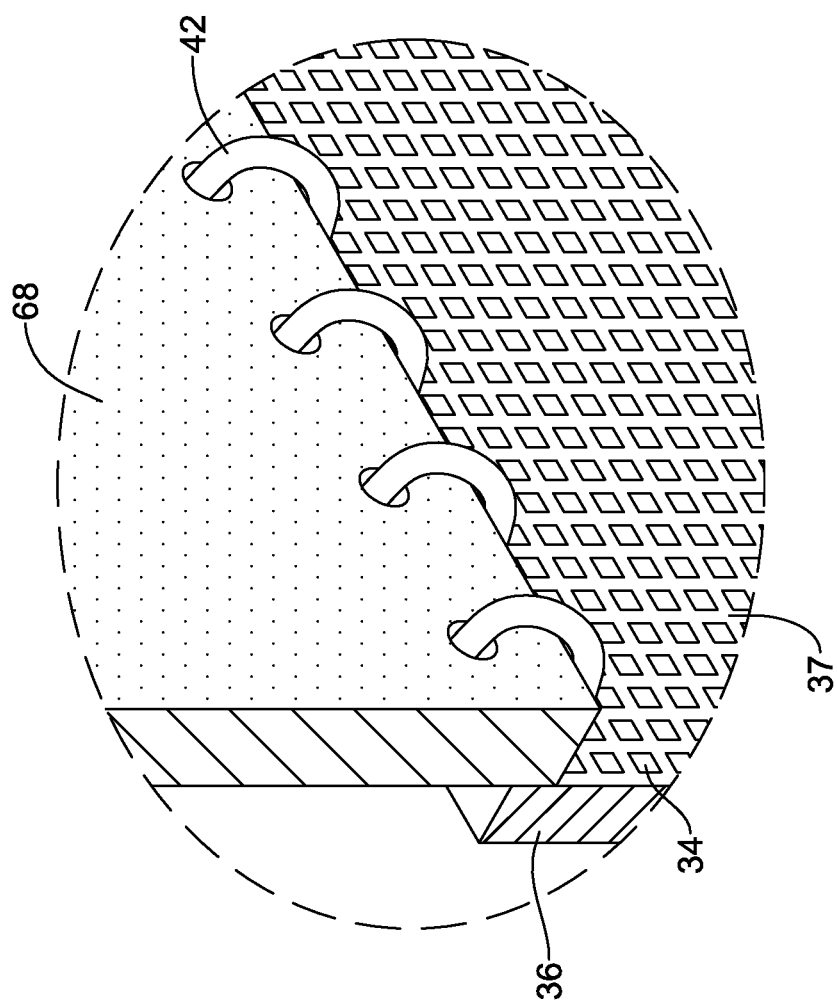
FIG. 4A illustrates a partial perspective view of aspects of the example medical implant shown in FIG. 3.
Figure 4B:
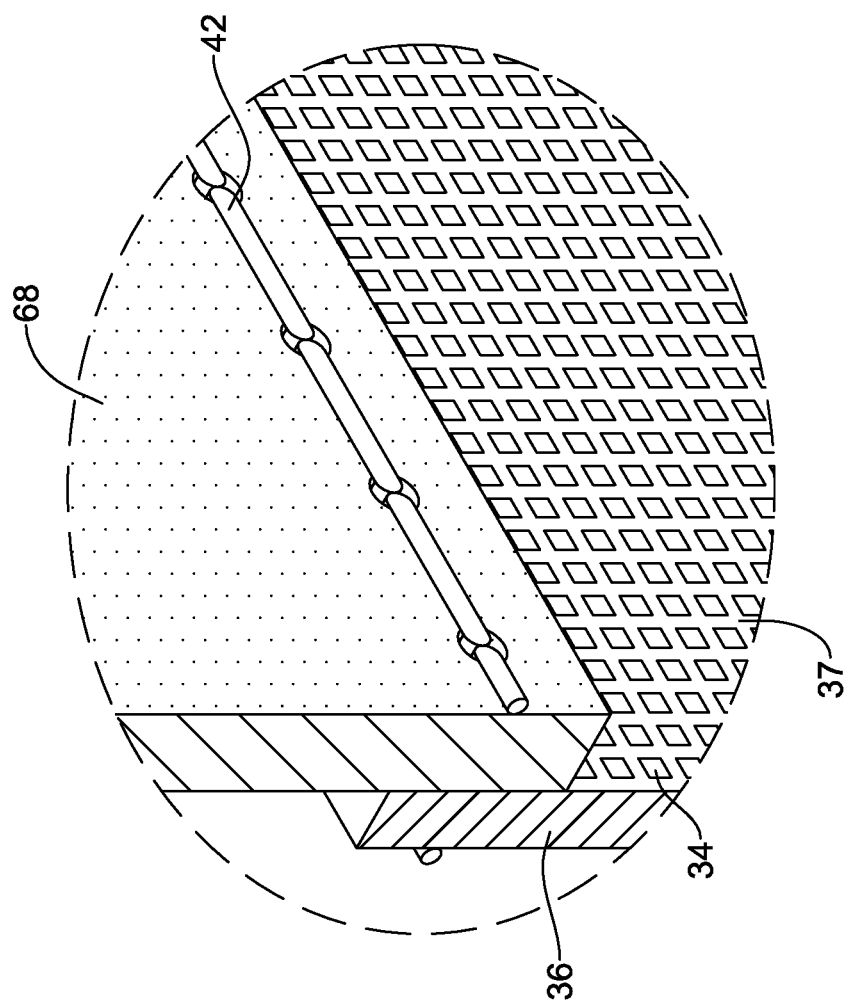
FIG. 4B illustrates a partial perspective view of aspects of the example medical implant shown in FIG. 3.

In some embodiments, at least one leaflet stitch 42 may secure the porous material 36, the blood-permeable material, and/or the fabric material to the plurality of valve leaflets 68. In some embodiments, the at least one leaflet stitch 42 may include at least one whip stitch, as shown in FIG. 4A. In some embodiments, the at least one leaflet stitch 42 may include a running stitch and/or a double running stitch, as shown in FIG. 4B. In some embodiments, the porous material 36, the blood-permeable material, and/or the fabric material may be further secured and/or attached to the plurality of valve leaflets 68 using an adhesive, a bonding agent, or other element(s).

Figure 5:
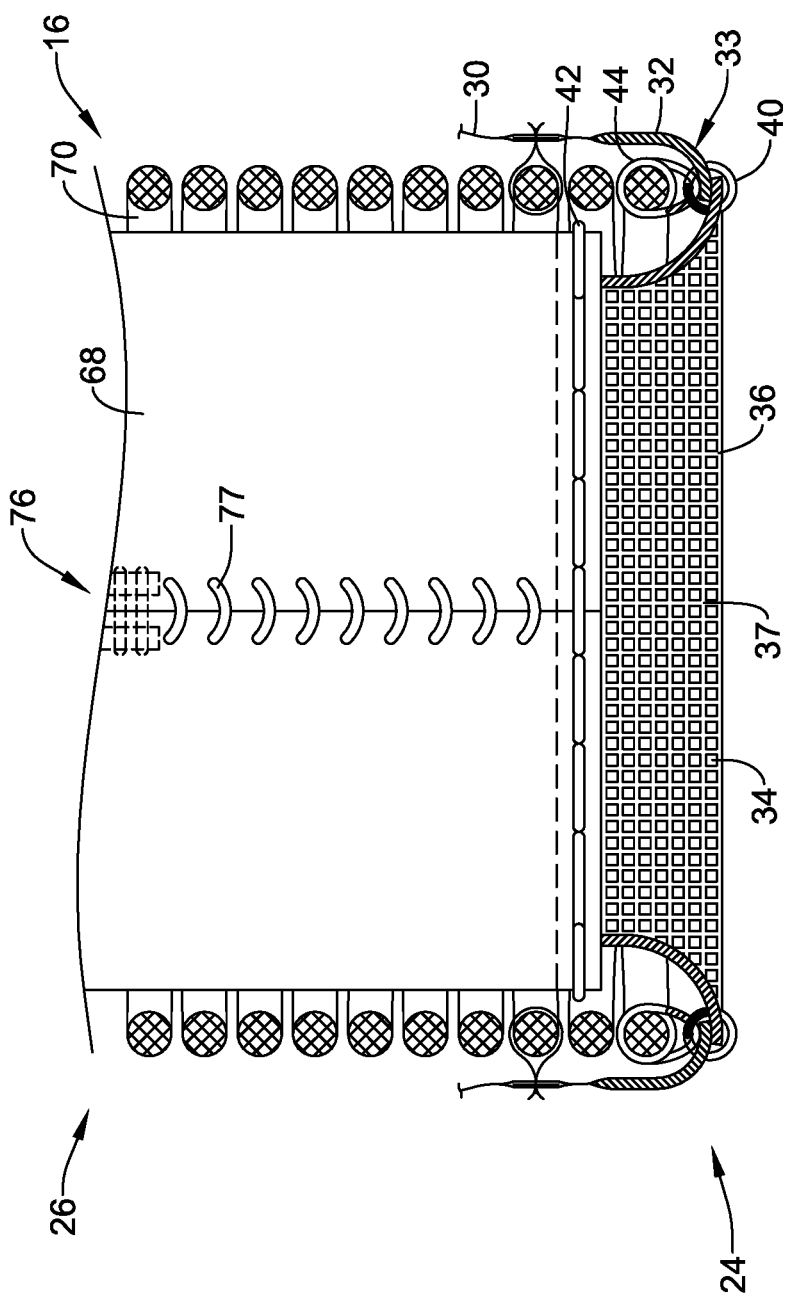
FIG. 5 is a partial cutaway view illustrating aspects of the example medical implant.

In the partial cutaway view of FIG. 5, a portion of the expandable anchor member 70 and elements outside of the expandable anchor member 70 have been removed to view aspects of the medical implant 16 disposed within the expandable anchor member 70. In this configuration, the plurality of valve leaflets 68 may have a substantially straight inflow is end. Adjacent leaflets of the plurality of valve leaflets 68 may be secured and/or attached together at a valve commissure axially aligned with one of the plurality of locking elements 76 by a whip stitch 77, which may be a helical suture for example. The adjacent leaflets of the plurality of valve leaflets 68 may be attached to the post member of the locking element 76 by the whip stitch 77 or by one or more commissure sutures. As may be seen in FIG. 5, the porous material 36, the blood-permeable material, and/or the fabric material may extend inside of the plurality of valve leaflets 68 proximate the inflow end of the plurality of valve leaflets 68. In some embodiments, the porous material 36, the blood-permeable material, and/or the fabric material may have a substantially constant longitudinal length or profile, as shown in FIG. 5. In at least some embodiments, the porous material 36, the blood-permeable material, and/or the fabric material may extend from the inflow end 24 of the expandable anchor member 70 and/or from the seal member 30 and/or the reinforcing band 32 to the valve commissure. The porous material 36, the blood-permeable material, and/or the fabric material may be joined to the plurality of leaflets 68 by the at least one leaflet stitch 42, which may be a running stitch, a double running stitch, or a helical whip stitch, as described herein.

In some embodiments, the porous material 36, the blood-permeable material, and/or the fabric material may have a sinusoidal or wave-like longitudinal length and/or profile. In this configuration, the plurality of valve leaflets 68 may also have a sinusoidal or wave-like inflow end corresponding to the porous material 36, the blood-permeable material, and/or the fabric material.

Figure 6:
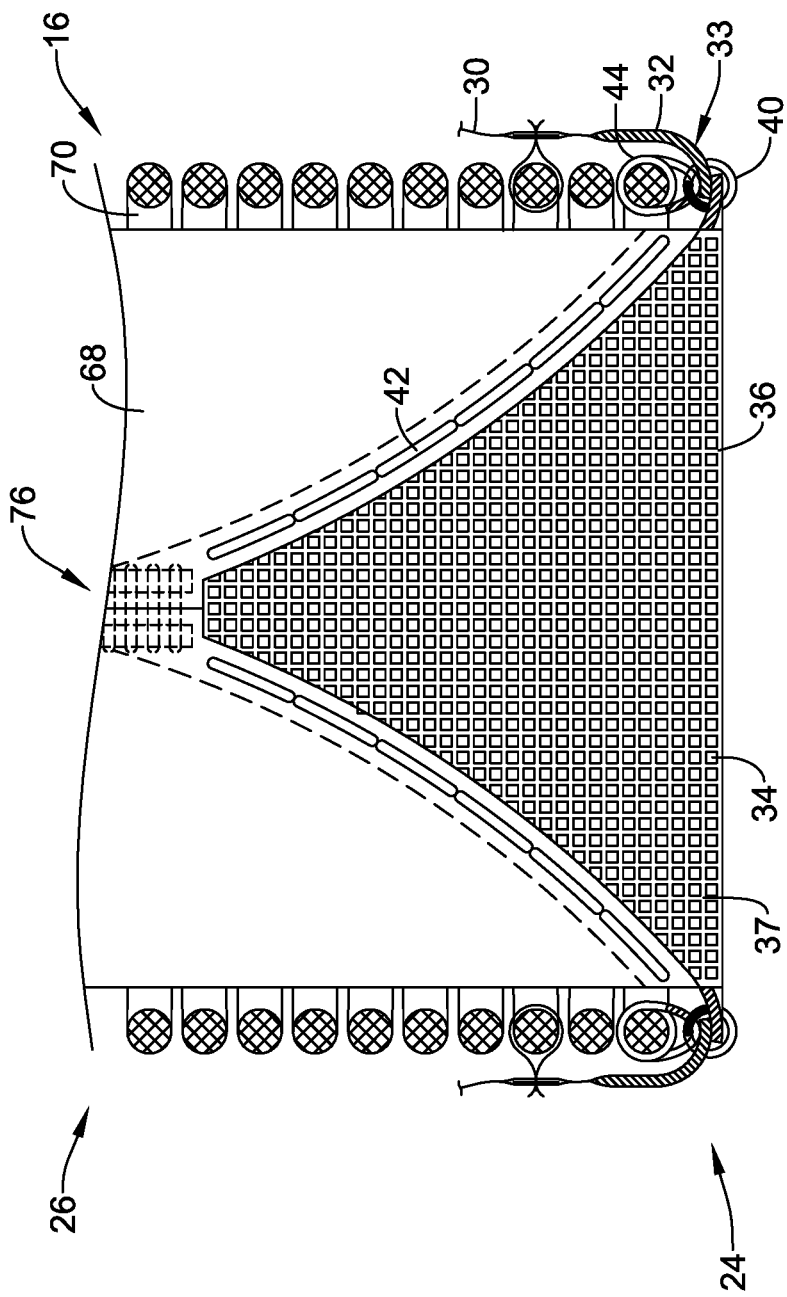
FIG. 6 is a partial cutaway view illustrating aspects of the example medical implant.

In the partial cutaway view of FIG. 6, a portion of the expandable anchor member 70 and elements outside of the expandable anchor member 70 have been removed to view aspects of the medical implant 16 disposed within the expandable anchor member 70. In this configuration, the plurality of valve leaflets 68 may have a generally V-shaped inflow end corresponding to the porous material 36, the blood-permeable material, and/or the fabric material, wherein the plurality of valve leaflets 68 is shortest at and/or adjacent the valve commissures and is longest at a circumferential location equidistant between adjacent valve commissures. The porous material 36, the blood-permeable material, and/or the fabric material may have a generally V-shaped longitudinal length and/or profile, as shown is in FIG. 6. The porous material 36, the blood-permeable material, and/or the fabric material may be longest directly below and/or axially aligned with the plurality of locking elements 76 and/or the valve commissures. This area generally sees the least amount of movement of the plurality of leaflets 68 during use. The medical implant 16 illustrated herein, may have three areas of the V-shaped profile, one for each valve commissure. However, other configurations are also contemplated. In some embodiments, at least a portion of the plurality of holes 34 and/or the porous material 36, the blood-permeable material, and/or the fabric material may extend along and/or within at least 25%, at least 35%, at least 45%, at least 50%, at least 60%, or more of an axial length of the expandable anchor member 70 in the "deployed" configuration and/or the "released" configuration.

Adjacent leaflets of the plurality of valve leaflets 68 may be secured and/or attached together at a valve commissure at one of the plurality of locking elements 76. The adjacent leaflets of the plurality of valve leaflets 68 may be attached to the post member of the locking element 76 by one or more commissure sutures. As may be seen in FIG. 6, the porous material 36, the blood-permeable material, and/or the fabric material may extend inside of the plurality of valve leaflets 68 proximate the inflow end of the plurality of valve leaflets 68. In at least some embodiments, the porous material 36, the blood-permeable material, and/or the fabric material may extend from the inflow end 24 of the expandable anchor member 70 and/or from the seal member 30 and/or the reinforcing band 32 to the valve commissure and/or the post member of the locking element 76. The porous material 36, the blood-permeable material, and/or the fabric material may be joined to the plurality of leaflets 68 by the at least one leaflet stitch 42, which may be a running stitch, a double running stitch, or a helical whip stitch, as described herein.

Figure 7:
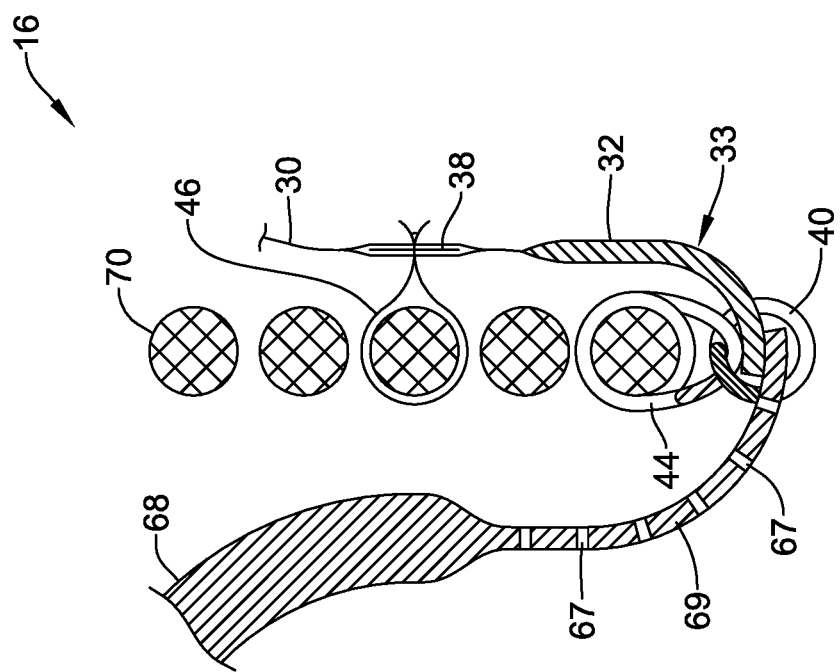
FIG. 7 is a partial section view illustrating aspects of the example medical implant.

In an alternative configuration, the medical implant 16 may include a thinned region 69 of the plurality of valve leaflets 68 (e.g., leaflet tissue) extending to and/or attached directly to the seal member 30 and/or the reinforcing band 32, as seen in FIG. 7. In some embodiments, the thinned region 69 of the plurality of valve leaflets 68 may include a plurality of holes 67 extending therethrough, thereby functioning similarly to the porous material 36, the blood-permeable material, and/or the fabric material described above. The plurality of holes 67 may permit fluid (e.g., blood) to flow through the lumen extending through the expandable anchor member 70 from the inflow side of the plurality of valve leaflets 68 to the outflow side of the plurality of valve leaflets 68 without passing through a lumen defined by the free edges of the plurality of valve leaflets 68. For example, the plurality of holes 67 may permit fluid (e.g., blood) to flow through the lumen extending through the expandable anchor member 70 from the inflow side of the plurality of valve leaflets 68 to the outflow side of the plurality of valve leaflets 68, from the outflow side of the plurality of valve leaflets 68 to the inflow side of the plurality of valve leaflets 68, or both, without passing through the plurality of valve leaflets 68 and/or without passing through the lumen defined by the free edges of the plurality of valve leaflets 68.

In some embodiments, the thinned region 69 of the plurality of valve leaflets 68 may be formed by applying pressure to a portion of the plurality of valve leaflets 68 using a press or other means. In some embodiments, a portion of each of the plurality of valve leaflets 68 may be compressed to reduce a thickness of the portion of each of the plurality of valve leaflets 68 by about 30%, about 40%, about 50%, about 60%, about 70% or more. In some embodiments, the thinned region 69 may have a thickness that is approximately ⅓ of the thickness of an un-thinned region of the plurality of valve leaflets 68. In one example, the plurality of valve leaflets may have a thickness of about 0.381 millimeters (about 0.0015 inches) and the thinned region 69 may have a thickness of about 0.127 millimeters (about 0.005 inches). Other configurations and/or thicknesses are also contemplated.

At least a portion of the thinned region 69 including the plurality of holes 67 is disposed within the lumen extending through the expandable anchor member 70. In some embodiments, the thinned region 69 including the plurality of holes 67 may have about 30% open area, about 35% open area, about 38% open area, about 40% open area, about 45% open area, etc. In some embodiments, the thinned region 69 including the plurality of holes 67 may have a longitudinal length measured parallel to the central longitudinal axis of about 3.0 millimeters, about 3.5 millimeters, about 3.8 millimeters, about 4.0 millimeters, about 4.2 millimeters, about 4.5 millimeters, about 5 millimeters, etc.

In some embodiments, the at least one seal stitch 40 may attach the reinforcing band 32 and/or the inflow end of the reinforcing band 32 to an inflow end of the thinned region 69 including the plurality of holes 67 and/or the plurality of valve leaflets 68 adjacent the inflow end of the expandable anchor member 70. In some embodiments, one or more inflow lashing sutures 44 may secure the at least one seal stitch 40, the inflow end of the thinned region 69 including the plurality of holes 67, the inflow end of the seal member 30, and/or the reinforcing band 32 to the expandable anchor member 70 at, proximate, and/or to the inflow end of the expandable anchor member 70. In at least some embodiments, the one or more inflow lashing sutures 44 may attach the at least one seal stitch 40, the inflow end of the thinned region 69 including the plurality of holes 67, the inflow end of the seal member 30, and/or the reinforcing band 32 to the strut(s), filament(s), and/or intersection(s) thereof of the expandable anchor member 70 disposed and/or positioned closest to the inflow end of the expandable anchor member 70.

In some embodiments, the one or more inflow lashing sutures 44 may directly attach the at least one seal stitch 40 to the inflow end of the expandable anchor member 70.

In some embodiments, the one or more inflow lashing sutures 44 may be interwoven with the at least one seal stitch 40 and/or a plurality of windings of the at least one seal stitch 40 to form a suture lattice. In some embodiments, at least a portion of the one or more inflow lashing sutures 44 may be looped through an interior of one or more of the plurality of windings of the at least one seal stitch 40 to form the suture lattice. In some embodiments, the one or more inflow lashing sutures 44 may form one or more second helical spirals oriented in a second direction about the inflow end of the expandable anchor member 70. In some embodiments, the one or more inflow lashing sutures 44 may form one or more second helical spirals oriented in a second direction about the inflow end of the expandable anchor member 70. In some embodiments, the first direction may be opposite the second direction.

As may be seen in FIG. 7, in at least some embodiments, the seal member 30 and/or the reinforcing band 32 does not pass through interstices in the expandable anchor member 70. In at least some embodiments, the thinned region 69 including the plurality of holes 67 does not pass through interstices in the expandable anchor member 70. Instead, the seal member 30, the reinforcing band 32, the thinned region 69 including the plurality of holes 67 may extend past and/or around the inflow end 24 of the expandable anchor member 70.

Figure 8:
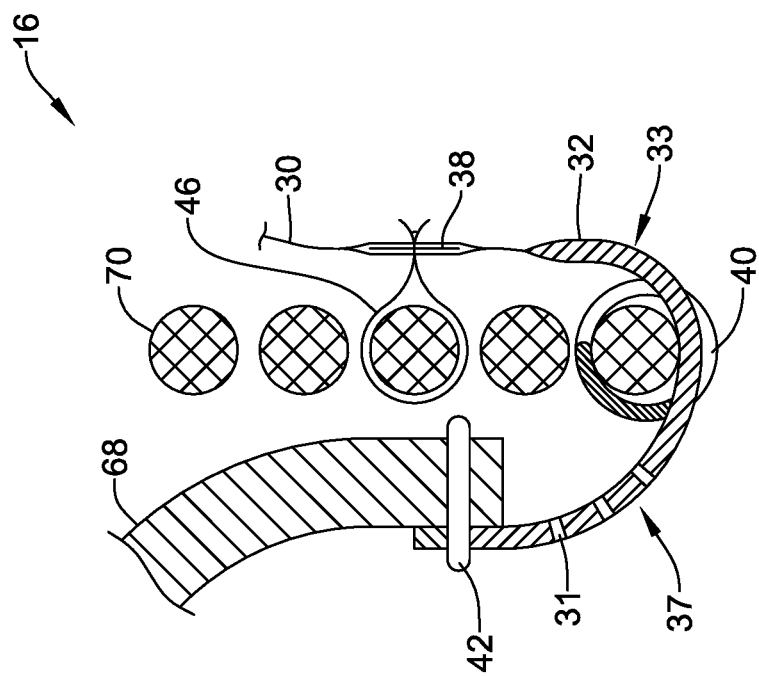
FIG. 8 is a partial section view illustrating aspects of the example medical implant.

In another alternative configuration, the seal member 30 and/or the reinforcing band 32 may extend into the lumen of the expandable anchor member 70 and attach directly to the plurality of valve leaflets 68, as seen in FIG. 8. In some embodiments, the seal member is 30 and/or the reinforcing band 32 may include a plurality of holes 31 extending therethrough within the lumen of the expandable anchor member 70, thereby functioning similarly to the porous material 36, the blood-permeable material, and/or the fabric material described above. The plurality of holes 31 may permit fluid (e.g., blood) to flow through the lumen extending through the expandable anchor member 70 from the inflow side of the plurality of valve leaflets 68 to the outflow side of the plurality of valve leaflets 68 without passing through the plurality of valve leaflets 68 and/or a lumen defined by the free edges of the plurality of valve leaflets 68. For example, the plurality of holes 31 may permit fluid (e.g., blood) to flow through the lumen extending through the expandable anchor member 70 from the inflow side of the plurality of valve leaflets 68 to the outflow side of the plurality of valve leaflets 68, from the outflow side of the plurality of valve leaflets 68 to the inflow side of the plurality of valve leaflets 68, or both, without passing through the plurality of valve leaflets 68 and/or without passing through the lumen defined by the free edges of the plurality of valve leaflets 68.

At least a portion of the seal member 30 and/or the reinforcing band 32 including the plurality of holes 31 is disposed within the lumen extending through the expandable anchor member 70. In some embodiments, the seal member 30 and/or the reinforcing band 32 including the plurality of holes 31 may have about 30% open area, about 35% open area, about 38% open area, about 40% open area, about 45% open area, etc. In some embodiments, a portion of the seal member 30 and/or the reinforcing band 32 including the plurality of holes 31 may have a longitudinal length measured parallel to the central longitudinal axis of about 3.0 millimeters, about 3.5 millimeters, about 3.8 millimeters, about 4.0 millimeters, about 4.2 millimeters, about 4.5 millimeters, about 5 millimeters, etc.

In some embodiments, the polymeric coating 33 of the seal member 30 and/or the reinforcing band 32 outside of the lumen of the expandable anchor member 70 is thicker than the polymeric coating 37 disposed within the lumen of the expandable anchor member 70. For example, the polymeric coating 33 of the seal member 30 and/or the reinforcing band 32 may close, plug, and/or seal off any holes, apertures, pores, and/or openings extending therethrough outside of the lumen of the expandable anchor member 70, while the plurality of holes 31 extending through the seal member 30 and/or the reinforcing band is 32 within the lumen of the expandable anchor member 70 may be at least partially unobstructed by the polymeric coating 37 thereon. In some embodiments, the polymeric coating 33 of the seal member 30 and/or the reinforcing band 32 may be at least about 30 microns thick, about 40 microns thick, about 50 microns thick, about 55 microns thick, about 60 microns thick, or another suitable thickness. In some embodiments, the polymeric coating 37 may be less than 10 microns thick, about 5 microns thick, about 3 microns thick, about 2 microns thick, about 1 micron thick, or another suitable thickness. For example, the entire seal member 30 and/or the entire reinforcing band 32 may comprise a polymeric coating thereon. In some embodiments, the polymeric coating may have different and/or varying thicknesses depending on where the polymeric coating is disposed on the seal member 30 and/or the reinforcing band 32. As noted herein, it is desirable for the plurality of holes 31 to remain at least partially unobstructed to facilitate fluid passage therethrough. The plurality of holes 31 is disposed between the inflow end of the expandable anchor member 70 and the inflow end of the plurality of valve leaflets 68, within the lumen of the expandable anchor member 70.

Similar to the configuration described above with respect to FIG. 3, at least one leaflet stitch 42 may secure the seal member 30 and/or the reinforcing band 32 to the plurality of valve leaflets 68 within the lumen of the expandable anchor member 70. In some embodiments, the at least one leaflet stitch 42 may include at least one whip stitch and/or at least one helical stitch (e.g., FIG. 4A). In some embodiments, the at least one leaflet stitch 42 may include a running stitch and/or a double running stitch (e.g., FIG. 4B). In at least some embodiments, an attachment region of the seal member 30 and/or the reinforcing band 32 to the plurality of valve leaflets 68 may have an increased thickness polymeric coating (e.g., polymeric coating 33) compared to the polymeric coating 37 disposed within the lumen of the expandable anchor member 70 to provide a more robust and/or durable attachment between the seal member 30 and/or the reinforcing band 32 and the plurality of valve leaflets 68. In some embodiments, the seal member 30 and/or the reinforcing band 32 may be further secured and/or attached to the plurality of valve leaflets 68 using an adhesive, bonding agent, or other element(s).

In some embodiments, the at least one seal stitch 40 may attach the seal member 30 and/or the reinforcing band 32 to the inflow end of the expandable anchor member 70 such is that the plurality of holes 31 is disposed within the lumen of the expandable anchor member 70. In some embodiments, the at least one seal stitch 40 may be at least one whip stitch or at least one helical stitch. In at least some embodiments, the at least one seal stitch 40 may attach the seal member 30 and/or the reinforcing band 32 to the strut(s), filament(s), and/or intersection(s) thereof of the expandable anchor member 70 disposed and/or positioned closest to the inflow end of the expandable anchor member 70.

As may be seen in FIG. 8, in at least some embodiments, the seal member 30 and/or the reinforcing band 32 does not pass through interstices in the expandable anchor member 70. In at least some embodiments, the seal member 30 and/or the reinforcing band 32 does not pass through interstices in the expandable anchor member 70. Instead, the seal member 30 and/or the reinforcing band 32 may extend past and/or around the inflow end of the expandable anchor member 70. Additionally, it is contemplated that the plurality of valve leaflets 68 and the seal member 30 and/or the reinforcing band 32 may have and/or take on any of the various arrangements illustrated in FIGS. 5-6, wherein the seal member 30 and/or the reinforcing band 32 may have a substantially constant longitudinal length, may have a sinusoidal or wave-like longitudinal length, and/or may have a generally V-shaped longitudinal length joined and/or attached directly to the plurality of valve leaflets 68 having a complimentary and/or corresponding length and/or shape.

FIG. 9 illustrates an alternative configuration for the plurality of holes 34 of the porous material 36, the blood-permeable material, and/or the fabric material discussed herein. In some embodiments, the plurality of holes 34 may have a variable size in a longitudinal direction. For example, the plurality of holes 34 may have a largest size proximate and/or adjacent the inflow end of the expandable anchor member 70, with the plurality of holes 34 gradually reducing in size in the longitudinal direction toward the plurality of valve leaflets 68 to a smallest size proximate and/or adjacent the inflow end of the plurality of valve leaflets 68. While expressly illustrated with respect to the plurality of holes 34, the same configuration may apply to the plurality of holes 67 of the thinned region 69 of the plurality of valve leaflets 68, as well as the plurality of holes 31 of the seal member 30 and/or the reinforcing band 32. Other configurations are also contemplated.

As a result of the aforementioned construction, the medical implant 16 may be is substantially sealed against fluid and/or blood flow around the exterior of the expandable anchor member 70 when positioned within the target site (e.g., the native valve) in the "deployed" configuration and/or the "released" configuration. The plurality of holes 34 of the porous material 36, the blood-permeable material, and/or the fabric material extending from the seal member 30 and/or the reinforcing band 32 to the plurality of valve leaflets 68, the plurality of holes 67 in the thinned region 69 of the plurality of valve leaflets 68, and/or the plurality of holes 31 in the seal member 30 and/or the reinforcing band 32 may provide one or more benefits to the function of the medical implant 16. For example, a pre-selected amount of fluid and/or blood may be permitted to flow through the plurality of holes 34, 67, 31. The pre-selected amount of fluid and/or blood may be selected to meet desired performance, anatomical, and/or regulatory requirements.

During the diastolic phase of the heartbeat, fluid and/or blood flow through the plurality of holes 34 of the porous material 36, the blood-permeable material, and/or the fabric material extending from the seal member 30 and/or the reinforcing band 32 to the plurality of valve leaflets 68, the plurality of holes 67 in the thinned region 69 of the plurality of valve leaflets 68, and/or the plurality of holes 31 in the seal member 30 and/or the reinforcing band 32 may serve to help "wash out" any fluid or blood that may be starting to stagnate behind the plurality of valve leaflets 68 in the cusps thereof (e.g., between the outflow side of the plurality of valve leaflets and the seal member 30 and/or the native valve annulus). This may help to prevent thrombus formation and/or release, which may have detrimental effects in/on other parts of the patient's anatomy. In some embodiments, the plurality of holes 34 of the porous material 36, the blood-permeable material, and/or the fabric material extending from the seal member 30 and/or the reinforcing band 32 to the plurality of valve leaflets 68, the plurality of holes 67 in the thinned region 69 of the plurality of valve leaflets 68, and/or the plurality of holes 31 in the seal member 30 and/or the reinforcing band 32 may alternatively and/or additionally reduce peak mechanical loads and/or strains applied to the expandable anchor member 70 during coaptation of the plurality of valve leaflets 68, thereby causing a damping effect during coaptation of the plurality of valve leaflets 68. Reducing peak mechanical loads and/or strains applied to the expandable anchor member 70, and/or the damping effect, may reduce wear and/or increase longevity of the expandable anchor member 70.

In another example, the plurality of holes 34 of the porous material 36, the blood-permeable material, and/or the fabric material extending from the seal member 30 and/or the reinforcing band 32 to the plurality of valve leaflets 68, the plurality of holes 67 in the thinned region 69 of the plurality of valve leaflets 68, and/or the plurality of holes 31 in the seal member 30 and/or the reinforcing band 32 may increase the effective orifice area (EOA) of the medical implant 16 by improving the flexibility and/or "hinge effect" of the plurality of valve leaflets 68 at the inflow end thereof when compared to medical implants lacking this feature and/or having valve leaflets secured directly to the expandable anchor member. The effective orifice area may be defined as the cross-sectional area through the lumen of the expandable anchor member 70 less the cross-sectional area through the lumen of the expandable anchor member 70 occupied by the plurality of valve leaflets 68 (e.g., the cross-sectional area through/within the plurality of leaflets 68 that is open to fluid flow during systole). The plurality of holes 34 of the porous material 36, the blood-permeable material, and/or the fabric material extending from the seal member 30 and/or the reinforcing band 32 to the plurality of valve leaflets 68, the plurality of holes 67 in the thinned region 69 of the plurality of valve leaflets 68, and/or the plurality of holes 31 in the seal member 30 and/or the reinforcing band 32 may permit the plurality of valve leaflets 68 to open faster and with less effort during systole, thereby reducing a pressure drop due to flow dynamics and/or minimizing the pressure gradient between inflow end and outflow end, which increases the effective orifice area when the Gorlin pressure equation is applied:

$$\text{Valve Area (cm}^2\text{)} = \frac{\text{Cardiac Output}\left(\frac{ml}{min}\right)}{\text{Heart rate}\left(\frac{beats}{min}\right) \cdot \text{Systolic ejection period (s)} \cdot 44.3 \cdot \sqrt{\text{mean Gradient (mmHg)}}}$$

The Gorlin equation states that the aortic valve area is equal to the flow through the aortic valve during ventricular systole divided by the systolic pressure gradient across the valve times a constant.

The materials that can be used for the various components of the medical device system 10 (and/or other systems disclosed herein) and the various elements thereof disclosed herein may include those commonly associated with medical devices. For simplicity purposes, the following discussion refers to the medical device system 10 and/or the medical implant 16. However, this is not intended to limit the devices and methods described herein, as the discussion may be applied to other elements, members, components, or devices disclosed herein, such as, but not limited to, the seal member 30, the reinforcing band 32, the polymeric coating 33, the porous material 36, the polymeric coating 37, the grommets 38, the sutures 40/42/44/46/77, the expandable anchor member 70, and/or elements or components thereof.

In some embodiments, the medical device system 10, the delivery system, and/or the medical implant 16, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be is distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties. In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10 and/or the medical implant 16 and/or other elements disclosed herein. For example, the medical device system 10 and/or the medical implant 16, and/or components or portions thereof, may be made of a material that does not substantially distort the image and create substantial artifacts (i.e., gaps in the image). Certain ferromagnetic materials, for example, may not be suitable because they may create artifacts in an MRI image. The medical device system 10 and/or the medical implant 16, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the medical device system 10 and/or the medical implant 16 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 10 and/or the medical implant 16 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyl s, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 10 and/or the medical implant 16 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical implant, comprising:
an expandable anchor member having a lumen extending through the expandable anchor member from an inflow end to an outflow end;
a plurality of valve leaflets disposed within the lumen extending through the expandable anchor member, the plurality of valve leaflets configured to move between an open configuration and a closed configuration;
a seal member disposed adjacent an exterior of the expandable anchor member; and
a porous material extending from the seal member to the plurality of valve leaflets, the porous material configured to allow fluid flow therethrough while the plurality of valve leaflets are in the closed configuration.

2. The medical implant of claim 1, wherein the seal member is disposed outside of the lumen extending through the expandable anchor member.

3. The medical implant of claim 1, wherein at least a portion of the porous material is disposed within the lumen extending through the expandable anchor member.

4. The medical implant of claim 1, wherein the seal member includes a reinforcing band disposed proximate the inflow end of the expandable anchor member.

5. The medical implant of claim 4, wherein the porous material extends from the reinforcing band to the plurality of valve leaflets.

6. The medical implant of claim 4, wherein the reinforcing band does not pass through interstices in the expandable anchor member.

7. The medical implant of claim 4, wherein the porous material does not pass through interstices in the expandable anchor member.

8. The medical implant of claim 1, wherein the porous material includes a polymeric coating.

9. A medical implant, comprising:
an expandable anchor member having a lumen extending through the expandable anchor member from an inflow end to an outflow end;
a plurality of valve leaflets disposed within the lumen extending through the expandable anchor member, the plurality of valve leaflets configured to move between an open configuration and a closed configuration;
a seal member disposed adjacent an exterior of the expandable anchor member; and
a fabric material extending from the seal member to the plurality of valve leaflets, the fabric material having a plurality of holes therethrough permitting fluid to flow between an inflow side of the plurality of valve leaflets and an outflow side of the plurality of valve leaflets without passing through the plurality of valve leaflets, while the plurality of valve leaflets are in the closed configuration.

10. The medical implant of claim 9, wherein at least one seal stitch secures the seal member to the fabric material.

11. The medical implant of claim 10, wherein the at least one seal stitch includes at least one whip stitch.

12. The medical implant of claim 9, wherein at least one leaflet stitch secures the fabric material to the plurality of valve leaflets.

13. The medical implant of claim 12, wherein the at least one leaflet stitch includes a running stitch.

14. The medical implant of claim 12, wherein the at least one leaflet stitch includes a double running stitch.

15. The medical implant of claim 12, wherein the at least one leaflet stitch includes at least one whip stitch.

16. A medical implant, comprising:
an expandable anchor member having a lumen extending through the expandable anchor member from an inflow end to an outflow end;
a plurality of valve leaflets disposed within the lumen extending through the expandable anchor member; and
a seal member disposed adjacent an exterior of the expandable anchor member and attached to the plurality of valve leaflets at the inflow end of the expandable anchor member;
wherein the plurality of valve leaflets each include a thinned region disposed proximate the inflow end of the expandable anchor member.

17. The medical implant of claim 16, wherein the thinned region includes a plurality of holes extending through the thinned region permitting fluid to flow between an inflow side of the plurality of valve leaflets and an outflow side of the plurality of valve leaflets without passing through a lumen defined by free edges of the plurality of leaflets.

18. The medical implant of claim 17, wherein the plurality of holes has a variable size.

19. The medical implant of claim 17, wherein the plurality of holes decreases in size in a direction from the inflow end of the expandable anchor member toward the outflow end of the expandable anchor member.

20. The medical implant of claim 16, wherein the thinned region does not pass through interstices in the expandable anchor member.

* * * * *